United States Patent
Kaula et al.

(10) Patent No.: US 9,610,449 B2
(45) Date of Patent: Apr. 4, 2017

(54) METHOD AND APPARATUS FOR DISPLAYING A GRAPHICAL IMPEDANCE HISTORY FOR OUTPUT CHANNELS OF A LEAD

(71) Applicant: Greatbatch Ltd., Clarence, NY (US)

(72) Inventors: Norbert Kaula, Arvada, CO (US); Yohannes Iyassu, Denver, CO (US)

(73) Assignee: Nuvectra Corporation, Plano, TX (US)

( * ) Notice: Subject to any disclaimer, the term of this patent is extended or adjusted under 35 U.S.C. 154(b) by 0 days.

(21) Appl. No.: 14/279,925

(22) Filed: May 16, 2014

(65) Prior Publication Data

US 2014/0343629 A1 Nov. 20, 2014

Related U.S. Application Data

(60) Provisional application No. 61/824,296, filed on May 16, 2013.

(51) Int. Cl.
| | |
|---|---|
| *A61N 1/372* | (2006.01) |
| *A61N 1/36* | (2006.01) |
| *G06F 3/0484* | (2013.01) |
| *G06F 3/0485* | (2013.01) |
| *G06F 19/00* | (2011.01) |

(52) U.S. Cl.
CPC ..... *A61N 1/37247* (2013.01); *A61N 1/36185* (2013.01); *G06F 3/0484* (2013.01); *G06F 3/0485* (2013.01); *G06F 3/04842* (2013.01); *G06F 19/3406* (2013.01); *G06F 19/3437* (2013.01); *G06F 19/3481* (2013.01)

(58) Field of Classification Search
CPC .......................... A61N 1/37247; G06F 3/0484
See application file for complete search history.

(56) References Cited

U.S. PATENT DOCUMENTS

| | | | | |
|---|---|---|---|---|
| 5,891,179 | A * | 4/1999 | Er et al. | 607/27 |
| 7,047,083 | B2 * | 5/2006 | Gunderson et al. | 607/116 |
| 2006/0224079 | A1 * | 10/2006 | Washchuk | 600/547 |
| 2006/0241721 | A1 * | 10/2006 | Kothandaraman et al. | 607/46 |
| 2007/0191911 | A1 * | 8/2007 | Greenberg | A61N 1/0543 607/54 |
| 2011/0307032 | A1 * | 12/2011 | Goetz et al. | 607/59 |
| 2014/0067020 | A1 * | 3/2014 | Kaula et al. | 607/60 |

* cited by examiner

*Primary Examiner* — Carl H Layno
*Assistant Examiner* — Jennifer Ghand
(74) *Attorney, Agent, or Firm* — Haynes and Boone, LLP; Eric Li

(57) ABSTRACT

Impedance information of an implantable medical device is displayed. One or more impedance values are received over a period of time for a plurality of channels. The channels may each include an electrode contact on an implantable lead. A graph is displayed that illustrates a variation of the impedance values over at least a portion of the period of time for one or more of the channels. A visual landscape that is representative of the impedance values for the plurality of channels is also displayed.

20 Claims, 12 Drawing Sheets

METHOD AND APPARATUS FOR DISPLAYING A GRAPHICAL IMPEDANCE HISTORY FOR OUTPUT CHANNELS OF A LEAD

PRIORITY DATA

The present application is a utility application of provisional U.S. Patent Application No. 61/824,296, filed on May 16, 2013, entitled "Features and Functionalities of an Advanced Clinician Programmer," the disclosure of which is hereby incorporated by reference in its entirety.

BACKGROUND

As medical device technologies continue to evolve, active implanted medical devices have gained increasing popularity in the medical field. For example, one type of implanted medical device includes neurostimulator devices, which are battery-powered or battery-less devices that are designed to deliver electrical stimulation to a patient. Through proper electrical stimulation, the neurostimulator devices can provide pain relief for patients or restore bodily functions.

Implantable medical devices (for example a neuro stimulator) can be controlled using an electronic programming device such as a clinician programmer or a patient programmer. These programmers can be used by medical personnel or the patient to define the particular electrical stimulation therapy to be delivered, via electrodes on an implantable lead, to a target area of the patient's body, alter one or more parameters of the electrical stimulation therapy, or otherwise conduct communications with a patient. Advances in the medical device field have improved these electronic programmers in certain aspects involving speed and user-friendliness. However, existing electronic programmers still have a variety of shortcomings. For example, existing programmers may not be able to provide detailed and intuitive impedance information for the electrodes on the lead. Without this impedance information, it may be difficult for healthcare professionals to effectively diagnose and treat the patient.

Therefore, although existing electronic programmers for controlling implantable medical devices have been generally adequate for their intended purposes, they have not been entirely satisfactory in every aspect.

SUMMARY

The present disclosure involves a method of displaying impedance information of an implantable medical device according to some embodiments. The method includes: receiving one or more impedance values over a period of time for a plurality of channels, wherein the channels each include an electrode contact on an implantable lead; displaying a graph that illustrates a variation of the impedance values over at least a portion of the period of time for one or more of the channels; and displaying a visual landscape that is representative of the impedance values for the plurality of channels.

The present disclosure involves an electronic device for displaying impedance information of an implantable medical device. The electronic device includes: a memory storage component configured to store programming code; and a computer processor configured to execute the programming code to perform the following tasks: receiving one or more impedance values over a period of time for a plurality of channels, wherein the channels each include an electrode contact on an implantable lead; displaying a graph that illustrates a variation of the impedance values over at least a portion of the period of time for one or more of the channels; and displaying a visual landscape that is representative of the impedance values for the plurality of channels.

The present disclosure involves a medical system. The medical system includes: an implantable lead configured to deliver electrical stimulation to a patient via one or more of a plurality of channels located on the implantable lead; and a portable electronic programmer on which a touch-sensitive user interface is implemented, wherein the user interface is configured to: receive one or more impedance values over a period of time for the plurality of channels; display a graph that illustrates a variation of the impedance values over at least a portion of the period of time for one or more of the channels; and display a visual landscape that is representative of the impedance values for the plurality of channels.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In the figures, elements having the same designation have the same or similar functions.

DETAILED DESCRIPTION

It is to be understood that the following disclosure provides many different embodiments, or examples, for implementing different features of the invention. Specific examples of components and arrangements are described below to simplify the present disclosure. These are, of course, merely examples and are not intended to be limiting. Various features may be arbitrarily drawn in different scales for simplicity and clarity.

In recent years, the use of active implanted medical devices has become increasingly prevalent. Some of these implanted medical devices include neurostimulator devices that are capable of providing pain relief by delivering electrical stimulation to a patient via electrodes (e.g., electrodes on an implantable lead). In that regards, electronic programmers have been used to configure or program these neurostimulators (or other types of suitable active implanted medical devices) so that they can be operated in a certain manner. These electronic programmers include clinician programmers and patient programmers, each of which may be a handheld device. For example, a clinician programmer allows a medical professional (e.g., a doctor or a nurse) to define the particular electrical stimulation therapy to be delivered to a target area of the patient's body, while a patient programmer allows a patient to alter one or more parameters of the electrical stimulation therapy.

Over the years, these electronic programmers have achieved significant improvements, for example, improvements in size, power consumption, lifetime, and ease of use. Nevertheless, the existing programmers still have various shortcomings. For example, existing programmers typically fail to provide the user detailed and intuitive impedance information for the channels of an implantable medical device. Without such impedance information, a healthcare professional may not be able to diagnose and treat the patient quickly.

The present disclosure offers an improved electronic programmer that overcomes the problems associated with existing electronic programmers. For example, the electronic programmer of the present disclosure is configured to display a graphical history of one or more channels of an implantable medical device, such as a pulse generator. The electronic programmer of the present disclosure is also configured to display a visual landscape that is representative of impedance values associated with the channels, which may provide a useful tool in making diagnosis and trouble-shooting. These various aspects of the electronic programmer of the present disclosure will be discussed in greater detail below with reference to FIGS. 1-12.

Figure 1:
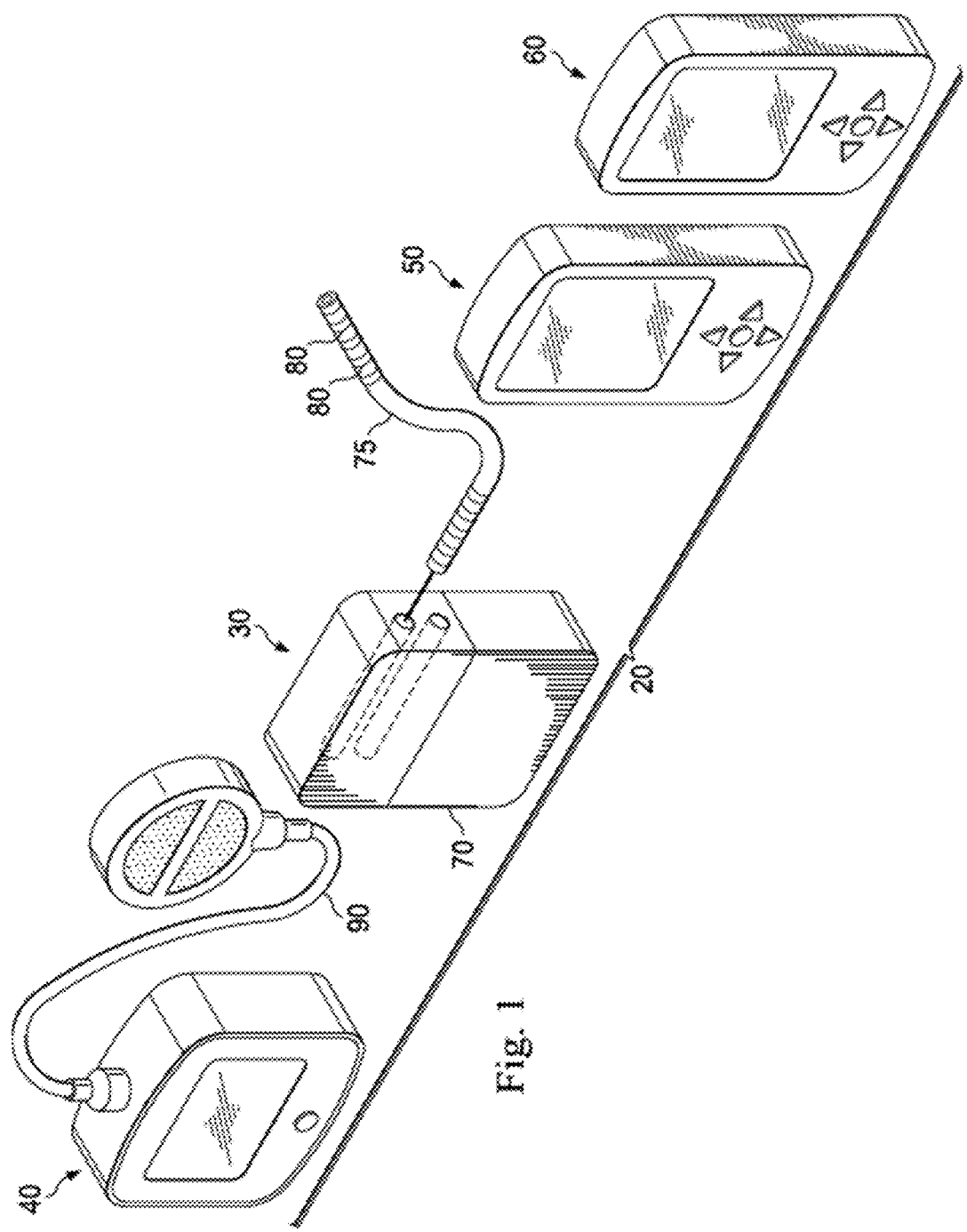
FIG. 1 is a simplified block diagram of an example medical environment in which evaluations of a patient may be conducted according to various aspects of the present disclosure.

FIG. 1 is a simplified block diagram of a medical device system 20 is illustrated to provide an example context of the various aspects of the present disclosure. The medical system 20 includes an implantable medical device 30, an external charger 40, a patient programmer 50, and a clinician programmer 60. The implantable medical device 30 can be implanted in a patient's body tissue. In the illustrated embodiment, the implantable medical device 30 includes an implantable pulse generator (IPG) 70 that is coupled to one end of an implanted lead 75. The other end of the implanted lead 75 includes multiple electrodes 80 (or electrode surfaces) through which electrical current is applied to a desired part of a body tissue of a patient. The implanted lead 75 incorporates electrical conductors to provide a path for that current to travel to the body tissue from the IPG 70. Although only one implanted lead 75 is shown in FIG. 1, it is understood that a plurality of implanted leads may be attached to the IPG 70.

Although an IPG is used here as an example, it is understood that the various aspects of the present disclosure apply to an external pulse generator (EPG) as well. An EPG is intended to be worn externally to the patient's body. The EPG connects to one end (referred to as a connection end) of one or more percutaneous, or skin-penetrating, leads. The other end (referred to as a stimulating end) of the percutaneous lead is implanted within the body and incorporates multiple electrodes analogous in function and use to those of an implanted lead.

The external charger 40 of the medical device system 20 provides electrical power to the IPG 70. The electrical power may be delivered through a charging coil 90. In some embodiments, the charging coil can also be an internal component of the external charger 40. The IPG 70 may also incorporate power-storage components such as a battery or capacitor so that it may be powered independently of the external charger 40 for a period of time, for example from a day to a month, depending on the power requirements of the therapeutic electrical stimulation delivered by the IPG.

The patient programmer 50 and the clinician programmer 60 may be portable handheld devices that can be used to configure the IPG 70 so that the IPG 70 can operate in a certain way. The patient programmer 50 is used by the patient in whom the IPG 70 is implanted. The patient may adjust the parameters of the stimulation, such as by selecting a program, changing its amplitude, frequency, and other parameters, and by turning stimulation on and off. The clinician programmer 60 is used by a medical personnel to configure the other system components and to adjust stimulation parameters that the patient is not permitted to control, such as by setting up stimulation programs among which the patient may choose, selecting the active set of electrodes in a given program, and by setting upper and lower limits for the patient's adjustments of amplitude, frequency, and other parameters. In some embodiments, patient programmers may include a patient programmer charger (PPC) and/or a pocket programmer (PoP).

In the embodiments discussed below, the clinician programmer 60 is used as an example of the electronic programmer. However, it is understood that the electronic programmer may also be the patient programmer 50 or other touch screen programming devices (such as smart-phones or tablet computers) in other embodiments.

Various features of the user interface of the clinician programmer 60 will now be described in detail below. In some embodiments, the user interface may be displayed on a screen of a programmer, for example a capacitive or resistive touch-sensitive display. In other embodiments, the user interface may be displayed on a programmer and an external monitor simultaneously, for example in accordance with U.S. patent application Ser. No. 13/600,875, filed on August 31, entitled "Clinician Programming System and Method", the disclosure of which is hereby incorporated by reference in its entirety. As such, both the healthcare provider and the patient are able to view the user interface at the same time.

Figure 2:
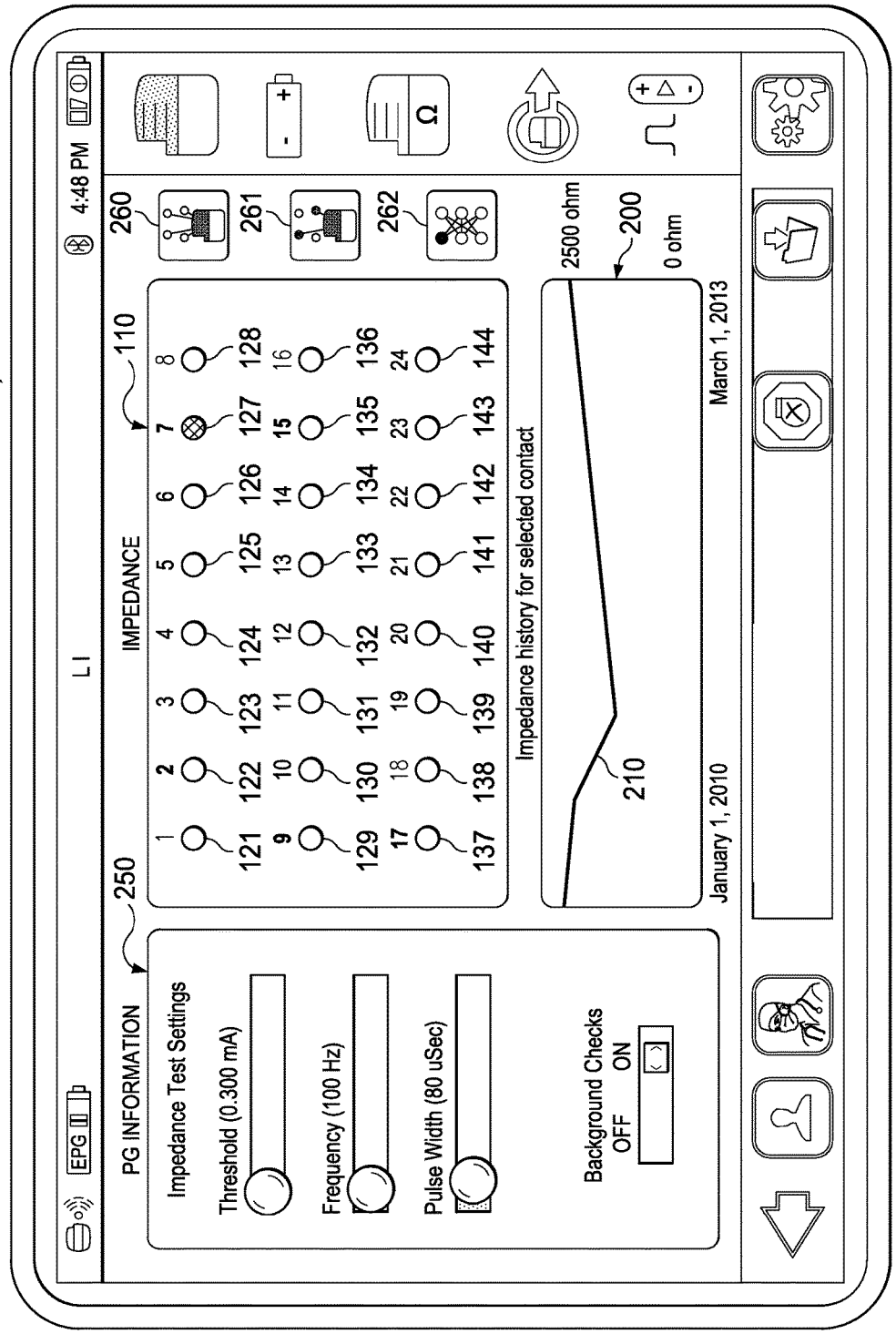
FIGS. 2-7 are graphical user interfaces on a clinician programmer according to various aspects of the present disclosure.

FIGS. 2-7 illustrate various portions of the user interface 100 displayed on the clinician programmer 60. Referring to FIG. 2, the user interface 100 includes a visual landscape 110 that is representative of impedance values of a plurality of output channels of an implantable medical device. In the illustrated embodiment, the implantable medical device includes 24 output channels. In other embodiments, the implantable medical device may include any number of output channels.

According to the various aspects of the present disclosure, it is desirable to monitor the impedance value (and the impedance history) of each channel. Generally, the impedance value for each channel is a summation of all of the impedance elements in series (for that channel). These impedance elements may include the IPG (e.g., the IPG 70 of FIG. 1), the lead body (e.g., the lead 75 of FIG. 1), the electrode contact (e.g., the electrode 80 of FIG. 1) on the lead, and/or body tissue. It is understood that most of these elements are resistive in nature, though the body tissue may contain reactive components and may behave more like an inductor or a capacitor, thereby causing the channel impedance to be a complex number. It is also understood although some of the elements (e.g., the IPG or the lead body) may be shared by the at least some of the channels, that each channel has its own electrode that is supposed to be electrically separated from other electrodes. It is through these electrodes that the impedance values of the channels are measured, as discussed in more detail later. For these reasons, the words "channel" and "electrode" may be used interchangeably hereinafter.

In the illustrated embodiment, the impedance information of the 24 output channels is visually portrayed by a plurality of icons 121-144, respectively. For example, channel 1 is represented by the icon 121, channel 2 is represented by the icon 122 . . . and channel 24 is represented by the icon 144. The icons 121-144 have visual characteristics that indicate the impedance range of the corresponding channel. For example, the icons 121-144 are color-coded to indicate the impedance of the channels 1-24. In some embodiments, a yellow color for the icon may indicate a low impedance range of the channel (i.e., below a predefined lower threshold), a red color for the icon may indicate a high impedance range of the channel (i.e., above a predefined upper threshold), and a green color for the icon may indicate a normal impedance range of the channel (i.e., between the upper and lower thresholds).

In some embodiments, the numbers 1 through 24 displayed above each of the icons 121-144 may be color-coded instead of, or in addition to, the icons 121-144. In yet other embodiments, the visual characteristic may include a non-color characteristic, such as a shape or texture of the icons 121-144. In some other embodiments, the icons 121-144 may include different types of symbols that each represent an impedance range of the corresponding channel. In further embodiments, the icons 121-144 may be replaced by (or be supplemented with) texts to directly indicate the impedance range of the corresponding channel.

In some embodiments, the impedance range discussed above includes a most recently measured impedance value for the channel. For example, suppose that the most recently measured impedance value for channel 1 may be from three days ago, (i.e., no impedance measurements have been performed since three days ago), and suppose that the measured impedance value for channel 1 is below the predefined lower threshold. As such, channel 1 is considered to have (or fall within) a low impedance range, and thus the icon 121 (or the text thereabove) will have a yellow color. Meanwhile, suppose that the most recently measured impedance value for channel 2 may be from two days ago, and that the measured impedance value for channel 2 is above the predefined upper threshold. As such, channel 2 is considered to have (or fall within) a high impedance range, and thus the icon 122 (or the text thereabove) will have a red color. In addition, suppose that the most recently measured impedance value for channel 3 is performed just a few moments ago (i.e., it was performed "on demand"), and that the measured impedance value for channel 3 below the predefined upper threshold and above the predefined lower threshold. As such, channel 3 is considered to have (or fall within) a normal impedance range, and thus the icon 123 (or the text thereabove) will have a green color.

In the examples discussed above, it can be seen that the most recently measured impedance values of the channels may come from different points in time. In other embodiments, the impedance values represented by the visual landscape 110 may be all taken substantially at the same point in time, for example during an impedance sweep for all the channels, which may be performed sequentially (i.e., one channel after another).

It is also understood that the impedance ranges do not necessarily include the most recently measured impedance values. In some embodiments, the impedance ranges for the channels may each include a worst case impedance value. For example, the impedance value for channel 9 may have been measured on a daily basis for the past week for a total of seven times. Each of the seven impedance values may be different from the rest. Rather than simply using the most recently measured impedance value for channel 9 as the impedance range to be represented by the icon 129, the worst case impedance value (regardless of the point in time it was measured) may be used. The worst case impedance value may be the greatest impedance value in some embodiments, or the lowest impedance value in other embodiments, or the greatest amount of deviation from either the upper threshold or from the lower threshold (indicating possibly an open condition or a short condition). In some other embodiments, the user may be allowed to define a time period and have the visual landscape 110 display the worst impedance value for each channel that comes from this particular time period. For example, several impedance sweeps may be performed for all the channels 1-24 during the past two days, and the visual landscape 110 may be configured to display the worst impedance value for each channel during the past two days.

Regardless, in these embodiments discussed above, the impedance ranges of each of the channels 1-24 (represented by the icons 121-144) may still correspond to an impedance value at a single point in time. In other words, each of the icons 121-144 indicates the impedance health for the corresponding channel at a snapshot in time, whatever that time may be. However, in some other embodiments, the impedance range for each channel may be based on a plurality of impedance values, for example as an average of all of (or a subset thereof) the impedance values obtained for that channel over a period of time.

Based on the above discussions, it can be seen that the visual landscape 110 lets the user quickly see which channels (or electrodes) are the problematic ones, since the problematic channels are visually portrayed by their corresponding visual characteristics (e.g., color) of the icons 121-144. For example, if the visual landscape 110 illustrates the icons 127 and 137 as red, then the user will know right away by looking at the visual landscape 110 that the channels 7 and 17 (corresponding to the icons 127 and 137, respectively) may have an electrical open condition. As another example, if the visual landscape 110 illustrates the icons 128 and 138 as yellow, then the user will know right away by looking at the visual landscape 110 that the channels 8 and 18 (corresponding to the icons 128 and 138, respectively) may have an electrical short condition. Trouble shooting may then be performed on these high impedance or low impedance channels. Meanwhile, green icons indicate that the underlying channel is behaving or functioning normally, and no further investigation may be necessary for the channels associated with these icons.

In addition, in the embodiments where the worst case impedance values are used to establish the visual landscape 110, the visual landscape 110 may help the user detect or catch intermittent faults. In some cases, the patient's bodily movement (i.e., shifting in position or posture, etc.) may cause one or more channels to occasionally exhibit a fault condition. For example, channel 15 may become loose and exhibit a higher-than-normal impedance indicating an electrical open condition, but this only occurs when the patient sits in a certain manner. If the patient assumes another position, the looseness of channel 15 may go away, and the impedance of channel 15 may appear to be in a normal range again. As another example, channel 16 may become shorted to ground (i.e., exhibiting a lower-than-normal impedance, for example an impedance approach zero) only when the patient lies down in a particular position. If the patient stands up or sits up, the electrical short condition may go away, and the impedance of channel 16 may appear to be in a normal range again.

In these scenarios discussed above, if only the most recent impedance value or an average impedance value is used to establish the visual landscape 110, the user (for example a healthcare professional) may miss these underlying fault conditions described above. However, if the worst case impedance values are used to establish the visual landscape 110, then the user may still be able to detect that the channels 15 and 16 are problematic, even if these problems are intermittent. In some cases, the user may instruct the patient to move his/her body or assume different positions and run an impedance test as the patient assumes each position. The plurality of impedance tests will yield worst case scenario impedance values for any problematic channels. These worst case scenario impedance values will be visually indicated by their corresponding icons in the visual landscape 110, thereby allowing the user to perform any necessary troubleshooting for that channel.

The user interface 100 also includes an impedance history graph 200. An X-axis of the graph 200 represents time, and a Y-axis of the graph 200 represents impedance. As such, the impedance history graph 200 graphically illustrates a variation of the impedance values for one or more of the channels over time. In some embodiments, this period of time is long enough for establish a meaningful impedance history for the selected channel, which may be a few days, a few weeks, a few months, or even a few years. In some embodiments, the impedance values for the channels are measured and sent (for example by the IPG) to the clinician programmer in response to queries generated by the clinician programmer. In other words, even if the clinician programmer has obtained a plurality of impedance values for one or more channels over time, each of these impedance values is obtained in response to a request from the clinician programmer. In other embodiments, however, the impedance values may be periodically measured (for example by the IPG) and automatically sent to the clinician programmer or a patient programmer each time they are measured.

The impedance history graph 200 may include one or more plots of impedance versus time, wherein each plot represents the impedance variation for a selected channel. In the embodiment shown in FIG. 2, the impedance history graph 200 includes an impedance plot 210. The impedance plot 210 includes a plurality of data points (i.e., impedance values) for a selected channel (for example channel 7) from Jan. 1, 2010 to Mar. 1, 2013. As shown in FIG. 2, the impedance changes (even if gradually) over this selected time period. Based on the observation of how the impedance values for channel 7 changed over time, the user may be able to make certain diagnoses accordingly.

It is understood that the X-axis and/or the Y-axis may be zoom-able and scrollable. For example, referring to FIG. 3, the user may zoom into a particular portion of both the X-axis and the Y-axis. Whereas the graph 200 in FIG. 2 displays the time period from Jan. 1, 2010 to Mar. 1, 2013 for the X-axis, and impedance from 0 ohm to 2500 ohms for the Y-axis, the graph 200 in FIG. 3 displays the time period from Apr. 9, 2012 to Mar. 1, 2013 for the X-axis, and the impedance from 2000 ohms to 2500 ohms for the Y-axis. In other words, both the X-axis and the Y-axis have been zoomed in for a more detailed display of the impedance values.

Figure 4:
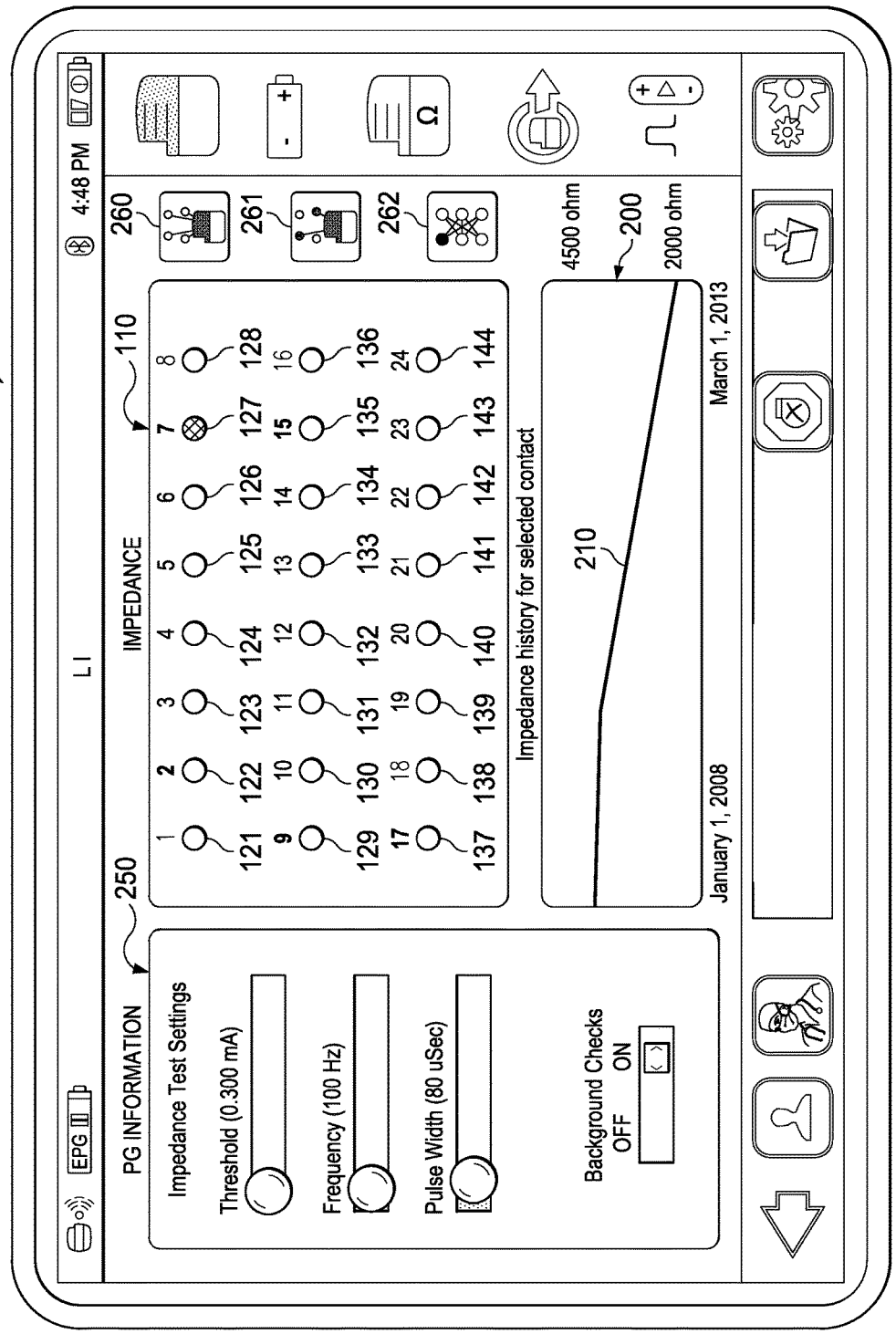
Figure 5:
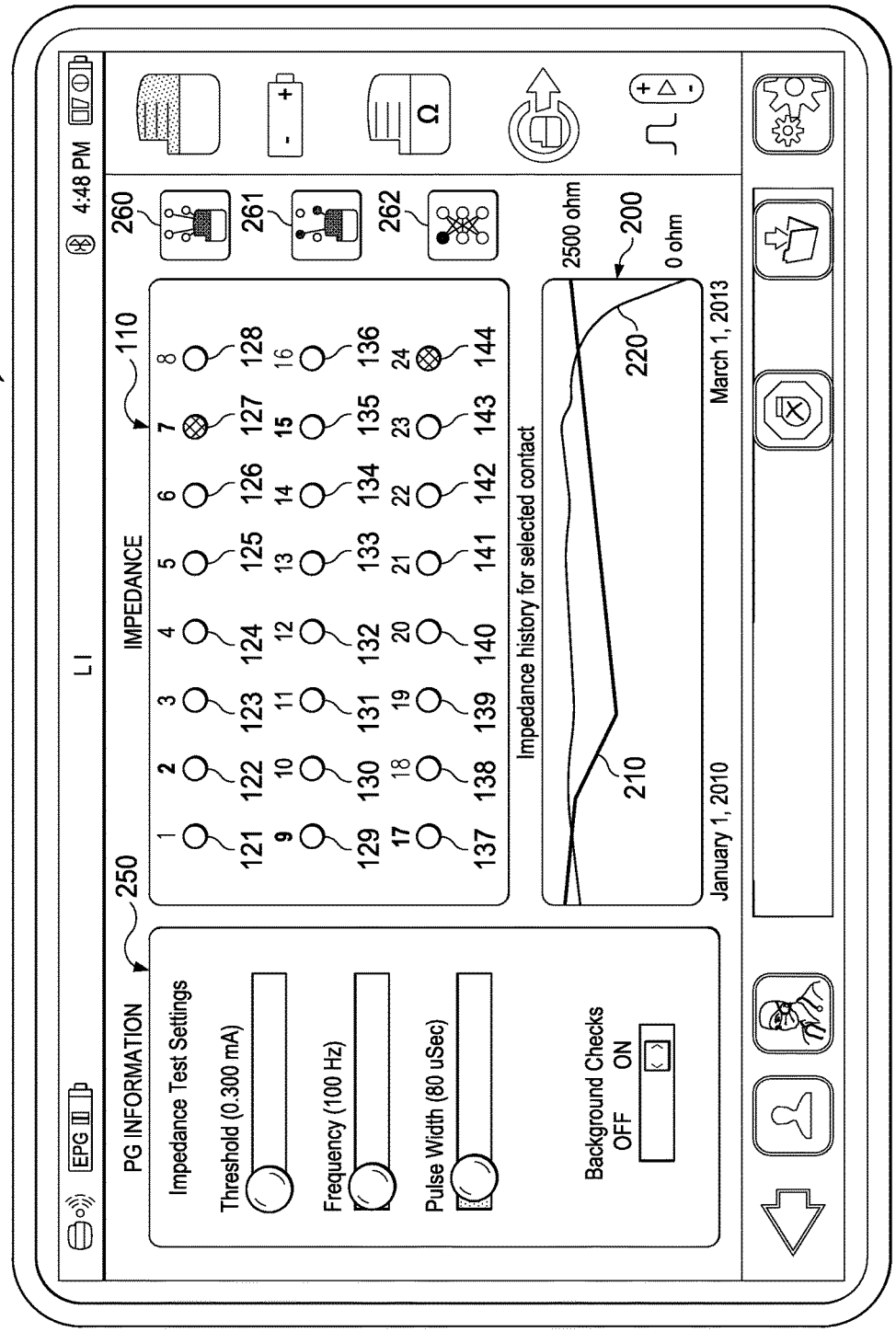

As another example, referring to FIG. 4, the user may scroll along the X-axis or the Y-axis. In this case, the X-axis has been scrolled back by two years such that the X-axis now corresponds to a time period from Jan. 1, 2008 to Mar. 1, 2011, and the Y-axis has been scrolled by 2000 ohms such that the Y-axis now corresponds to an impedance range from 2000 ohms to 4500 ohms.

In some embodiments, the zooming and the scrolling operations discussed above may be performed via a touch-based engagement with the graphical user interface 100. For example, the user may perform a pinch gesture to the user interface 100 to perform the zooming, and a swipe gesture to the user interface to perform the scrolling. In other embodiments, the zooming and scrolling may be performed via virtual icons (not illustrated herein) on the user interface 100, such as + and − signs for zooming in and out, or arrows pointing at a given direction for scrolling along that direction. In yet other embodiments, traditional user input/output mechanism such as a mouse or a keyboard may also be used to perform the zooming and scrolling. Regardless of the mechanism used to accomplish the zooming and scrolling of the X and Y axes, it can be seen that they allow the user to focus in on a particular region on the graph 200 that is of interest to the user, thereby facilitating the user's diagnosis of the patient.

Figure 3:
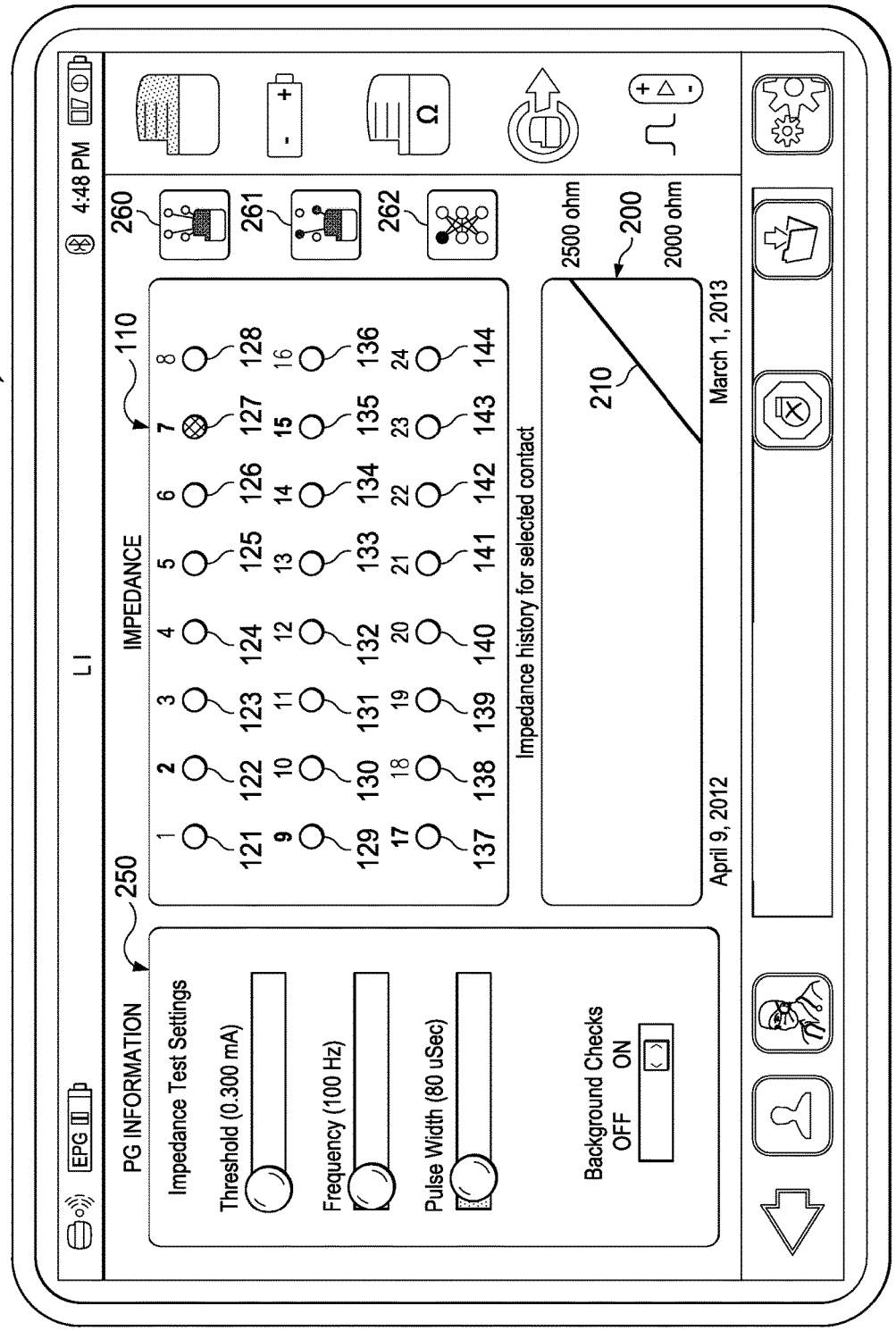

In FIGS. 2-4, the impedance history graph 200 includes only one impedance plot 210 for a single selected channel. However, it is understood that the impedance history graph 200 may allow a plurality of impedance plots to be displayed concurrently, wherein each of the impedance plots corresponds to a different channel's impedance variation over time. For example, referring now to FIG. 5, in addition to displaying the impedance plot 210 for the channel 7, the impedance history graph 200 also displays an impedance plot 220 for the channel 24. It can be seen that the impedance values for the channel 24 do not change very much until close to Mar. 1, 2013, where it begins to dive toward zero. At Mar. 1, 2013, the impedance value of channel 24 has substantially reached zero ohms (as indicated by the plot 220). In other words, the channel 24 was performing well until a few months before Mar. 1, 2013, but by Mar. 1, 2013, it has likely been shorted. The illustrated graphical impedance variation over time for both channels 7 and 24 therefore allows the user to make accurate diagnoses for multiple channels at a time.

The graphical user interface 100 also contains a plurality of virtual buttons and/or windows to carry out the impedance measurement and display. For example, the user interface 100 includes a virtual window 250. The window 250 contains user-configurable settings for a test pulse used to perform an impedance test, such as pulse amplitude, frequency, and pulse width. In more detail, to measure the impedance of any given channel, a test electrical pulse (e.g., a current pulse) is sent through the channel via the implantable medical device (e.g., the IPG 70). Knowing the voltage and the current, impedance can be calculated via Ohm's law $V=I*Z$, where V is voltage, I is current, and Z is impedance. Note that the above equation applies when one or more of the variables are in complex form, as is the case in the context of impedance measurements inside a human body. When the variables are real, then Ohm's law can be expressed a $V=I*R$, where R is resistance.

These settings in the virtual window 250 help the user define an appropriate test pulse for impedance measurements. If the test electrical pulse is too strong, the patient may experience pain or other uncomfortable sensations. If the test electrical pulse is too weak, the impedance result may not be as accurate as needed. Therefore, the virtual window 250 allows the user to configure the settings of the test pulse in order to generate a desired test pulse that can competently perform the impedance measurement, while also minimizing patient discomfort. It is also understood that in some embodiments, the settings in the virtual window 250 may be simplified to reduce possible user confusion.

The graphical user interface 100 may also contain virtual buttons 260-262. In the illustrated embodiment, a user engagement with the virtual button 260 triggers an impedance sweep for all of the channels, a user engagement with the virtual button 261 triggers an impedance sweep for a subset of the channels that are selected, and a user engagement with the virtual button 262 causes a list of impedance values to be displayed, for example as shown in FIG. 6.

Figure 6:
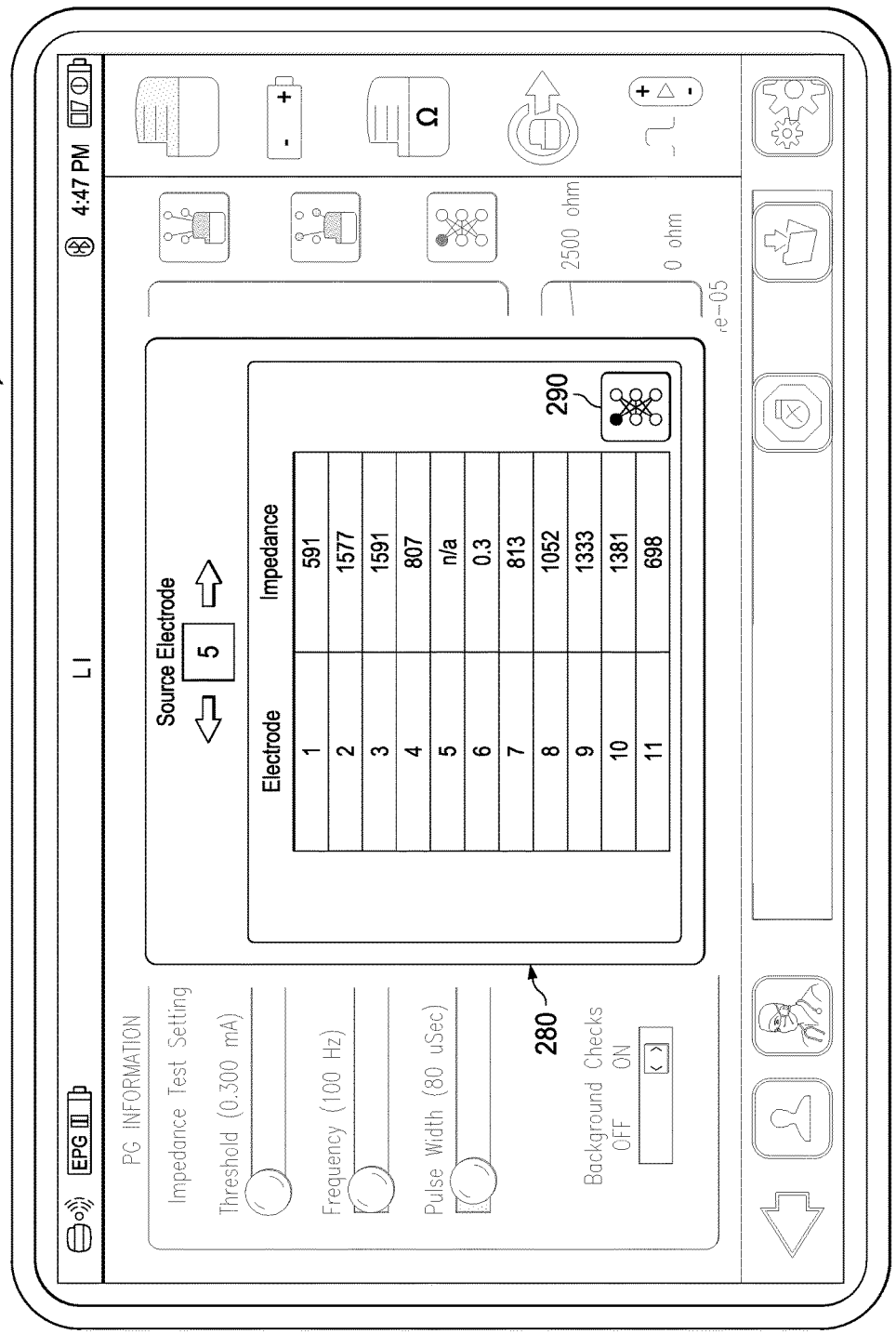

Referring to FIG. 6, the user engagement with the virtual button 262 triggers the display of a pop-up window 280. The pop-up window 280 displays a list of channels (labeled as "electrode" in the window 280) and the respective impedance values associated with the channels in a table form. The list of channels displayed may include all of the channels, or just a subset of the channels. In some embodiments, the impedance being displayed alongside each channel in the window 280 may be the impedance value of that channel measured with respect to a selected channel, also referred to as source electrode. In the illustrated embodiment, the selected channel (labeled as "source electrode") is channel 5. As such, the impedance value between channel 5 and channel 1 is displayed alongside channel 1, the impedance value between channel 5 and channel 2 is displayed alongside channel 2, so on and so forth. The impedance value next to channel 5 is displayed as "n/a" (i.e., not applicable), since channel 5 is the source channel itself.

The user may also click on the left or right arrows next to the "source electrode" to change the source channel. For example, if the left arrow is clicked, the source channel is changed to channel 4, whereas if the right arrow is clicked, the source channel is changed to channel 6. A new impedance sweep may then be performed with respect to the new source channel. In some embodiments, the new impedance sweep is automatically triggered as soon as the user changes the source channel. In other embodiments, the new impedance sweep is performed in response to the user pressing a virtual button 290.

Figure 7:
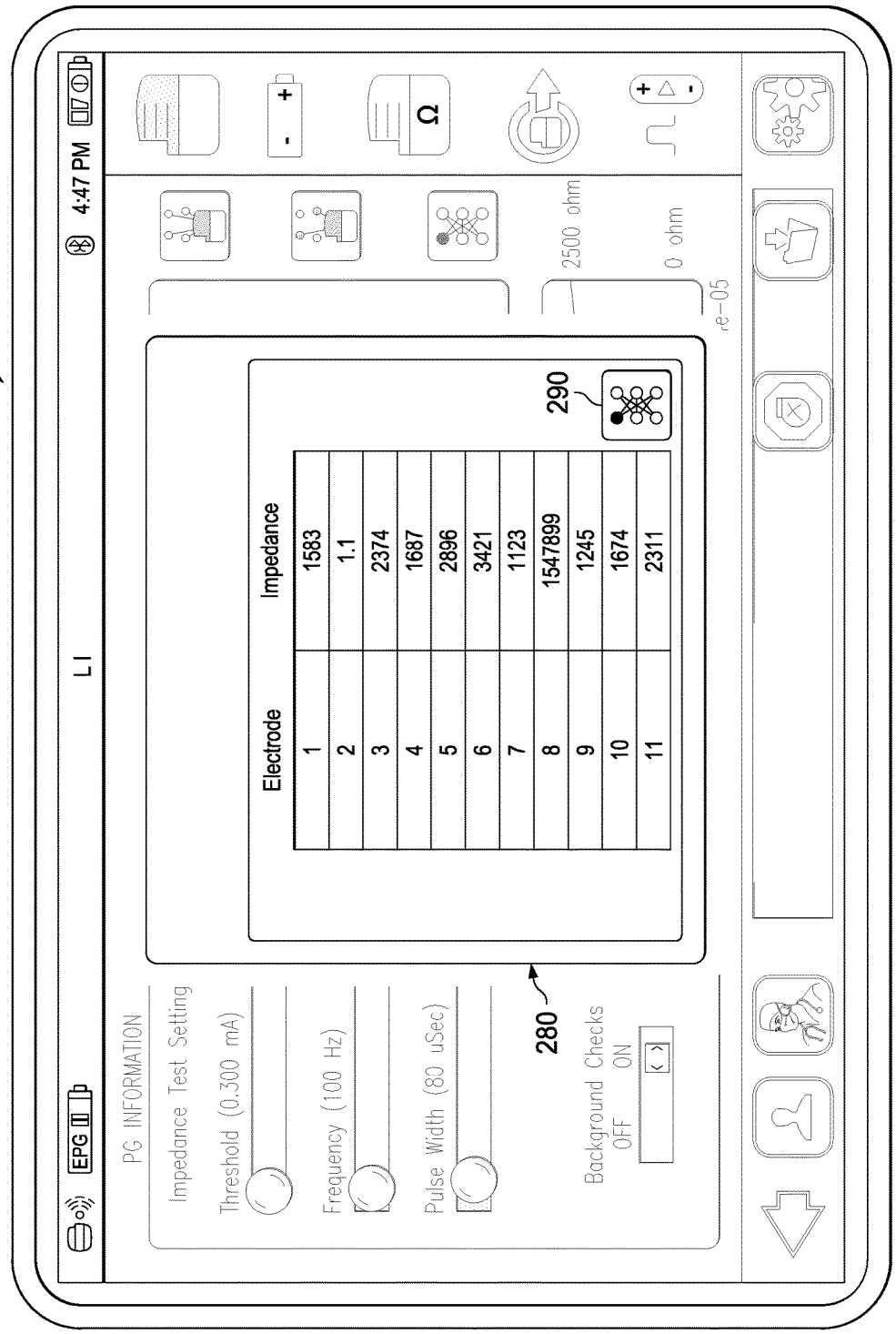

In other embodiments, the impedance being displayed alongside each channel in the window 280 may be the impedance value of that channel measured with respect to electrical ground. An example of this embodiment is shown in FIG. 7, where the impedance values (measured with respect to ground) are displayed for channels 1-11, respectively. Again, the channels 1-11 may merely be a selected subset of the total number of channels. The impedance sweep with respect to ground may be performed for all channels, or just the selected subset of the channels.

The list of impedance values in the pop-up window 280 in FIG. 6-7 can quickly convey important information to the user. For example, in the embodiment shown in FIG. 6, the user can quickly determine if there is a short circuit between two of the electrodes by looking at the list of impedance values. Under normal conditions, there should be a healthy amount of impedance between any two of the channels, for example an impedance ranging from a few hundred ohms to a few thousand ohms. If there is a short circuit between two of the channels, however, the impedance between these two channels will substantially approach zero. For example, in FIG. 6, the impedance value displayed next to channel 6 is 0.3 ohms, meaning that the impedance between channel 6 and the source channel 5 is 0.3 ohms. This number is close enough to zero to likely indicate a short circuit between channels 5 and 6, and the user (i.e., healthcare professional) may need to investigate channels 5 and 6 to further determine what corrective measures need to be taken.

On the other hand, in the embodiment shown in FIG. 7, the user can quickly determine if there is a short circuit or open circuit condition for each of the channels by looking at the list of impedance values. Again, under normal conditions, there should be a healthy amount of impedance between any channel (that is active) and ground, for example an impedance ranging from a few hundred ohms to a few thousand ohms. If any of the channels is shorted to ground, however, the impedance value for that channel will substantially approach zero. On the other hand, if any of the channels becomes electrically open (e.g., the lead being unplugged), the impedance value for that channel will be extremely high, for example in the range of hundreds of kilo-ohms or mega-ohms. In the example shown in FIG. 7, the impedance value displayed next to channel 2 is 1.1 ohms, meaning that the impedance between channels 2 and ground is 1.1 ohms. This number may be close enough to zero to likely indicate that channel 2 has been shorted to ground. In addition, the impedance value displayed next to channel 8 is 1547899 ohms, which is a very high impedance value. This high impedance value may indicate that channel 8 has become electrically open for whatever reason. Based on such information, the user (i.e., healthcare professional) may need to investigate channels 2 and 8 to further determine what corrective measures need to be taken.

In some embodiments, if an impedance value is outside of a predefined range (in other words, it is too high or too low), an alert or notification may be generated automatically. The alert may be displayed via the graphical user interface, or it may be audibly announced by speakers of the clinician programmer. The automatic generation of the alert further ensures that any underlying fault conditions associated with any of the channels will be caught.

Figure 8:
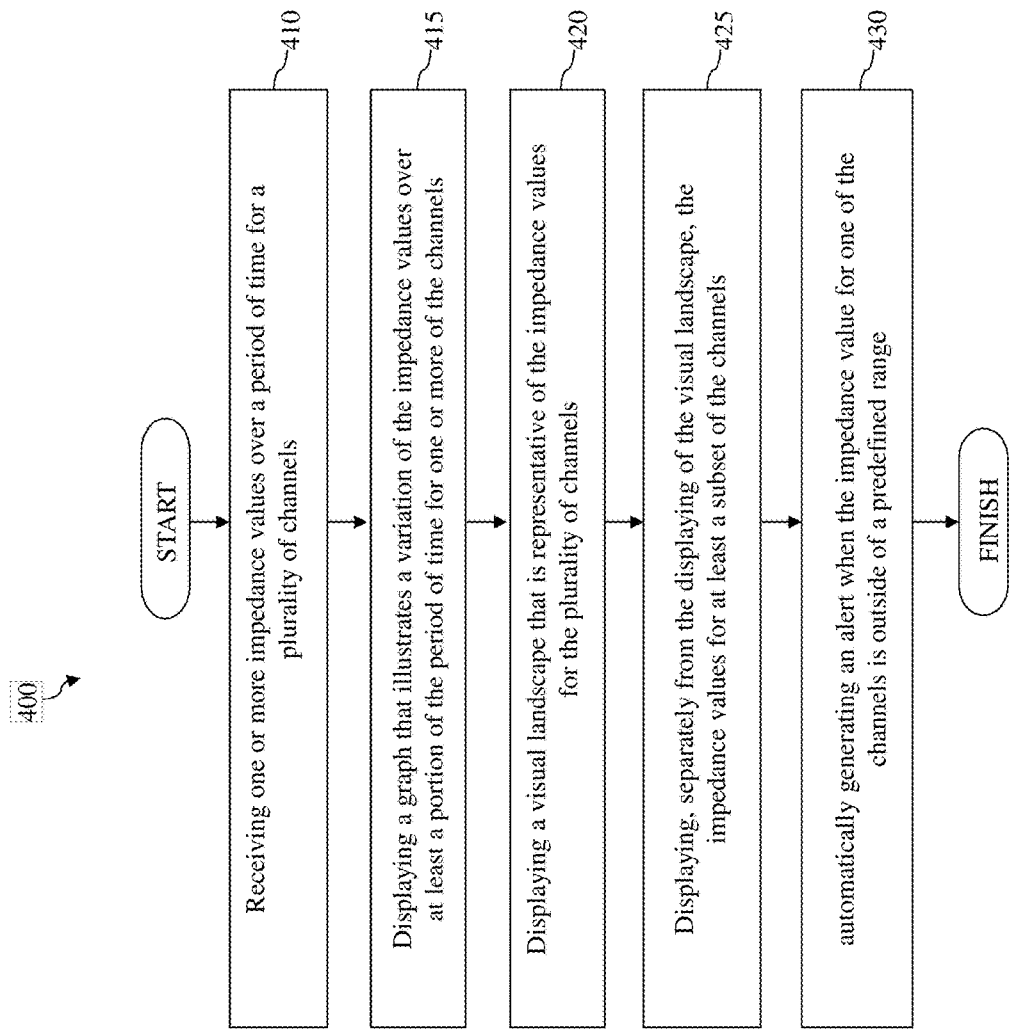
FIG. 8 is a flowchart illustrating example process flows for displaying impedance information according to various aspects of the present disclosure.

FIG. 8 is a simplified flowchart of a method 400 of displaying impedance information of an implantable medical device. The method 400 includes a step 410 of receiving one or more impedance values over a period of time for a plurality of channels. The channels each include an electrode contact on an implantable lead.

The method 400 includes a step 415 of displaying a graph that illustrates a variation of the impedance values over at least a portion of the period of time for one or more of the channels. In some embodiments, the displaying of the graph comprises displaying, concurrently on the graph: a first plot representing the variation of the impedance values for a first one of the channels over the period of time; and a second plot representing the variation of the impedance values for a second one of the channels over the period of time. In some embodiments, the displaying of the graph is performed such that the graph includes a X-axis representing time and a Y-axis representing impedance. At least one of the X-axis and the Y-axis may be zoom-able or scrollable.

The method 400 includes a step 420 of displaying a visual landscape that is representative of the impedance values for the plurality of channels. In some embodiments, the step 420 of displaying of the visual landscape comprises displaying a plurality of icons that are each associated with a respective one of the channels. A visual characteristic of each of the icons indicates an impedance value range of the channel associated with the icon. In some embodiments, the visual characteristic comprises color, and a color of each icon represents the impedance value range of the channel associated with the icon. In some embodiments, the impedance value range includes a most recent impedance value for the channel associated with the icon. In some embodiments, the impedance value range includes an average of one or more of the plurality of impedance value for the channel associated with the icon.

The method 400 includes a step 425 of displaying, separately from the displaying of the visual landscape, the impedance values for at least a subset of the channels. In some embodiments, each of the impedance values is measured with respect to ground. In some embodiments, each of the impedance values is measured with respect to each of the rest of the channels in the subset.

The method 400 includes a step 430 of automatically generating an alert when the impedance value for one of the channels is outside of a predefined range.

In some embodiments, one or more of the steps 410-430 may be performed by a clinician programmer. In some embodiments, the clinician programmer has a touch-sensitive graphical user interface, and one or more of the steps 410-430 may be performed at least in part via the touch-sensitive graphical user interface.

It is understood that the steps 410-430 need not be performed sequentially. Furthermore, additional steps may be performed before, during, or after the steps 410-430. For example, the method 400 may include a step of displaying a window showing one or more user-configurable settings for generating an electrical pulse used to perform impedance measurements for the plurality of channels.

Based on the discussions above, it can be seen that the clinician programmer of the present disclosure is capable of displaying impedance information of the channels of an implantable device. By doing so, the clinician programmer of the present disclosure facilitates diagnosis and troubleshooting of problems. In more detail, after surgery, the impedance history for each channel usually follows an expected pattern if all is normal. However, if there are mechanical problems, the impedance history will reflect these problems. For example, if an abnormally high impedance is observed, that corresponds to an open circuit condition, which may indicate a lead has been snapped (or another potential open circuit in the channel). On the other hand, if an abnormally low impedance is observed, that indicates a short circuit condition, which may indicate a wire in the lead is touching another wire (or another potential short circuit in the channel). The healthcare professional may then try to repair the channel to fix the problem indicated by the impedance history.

It is noted that for mechanical problems such as open/short circuit conditions discussed above, the change in impedance usually will be dramatic. However, if the impedance history does not have a dramatic variation but nevertheless deviates from an expected pattern, then that may indicate an underlying problem with the tissue. For example, if the tissue is being inflamed, the impedance may experience a drop over time. Such drop in impedance may not be dramatic but is still noticeable to indicate a problem exists. Similarly, other problems with the tissue may manifest themselves in various impedance history patterns. Therefore, the impedance history may be used to not only discover and trouble a mechanical problem with the channel, but also an underlying condition for the tissue that needs to be addressed.

Figure 9:
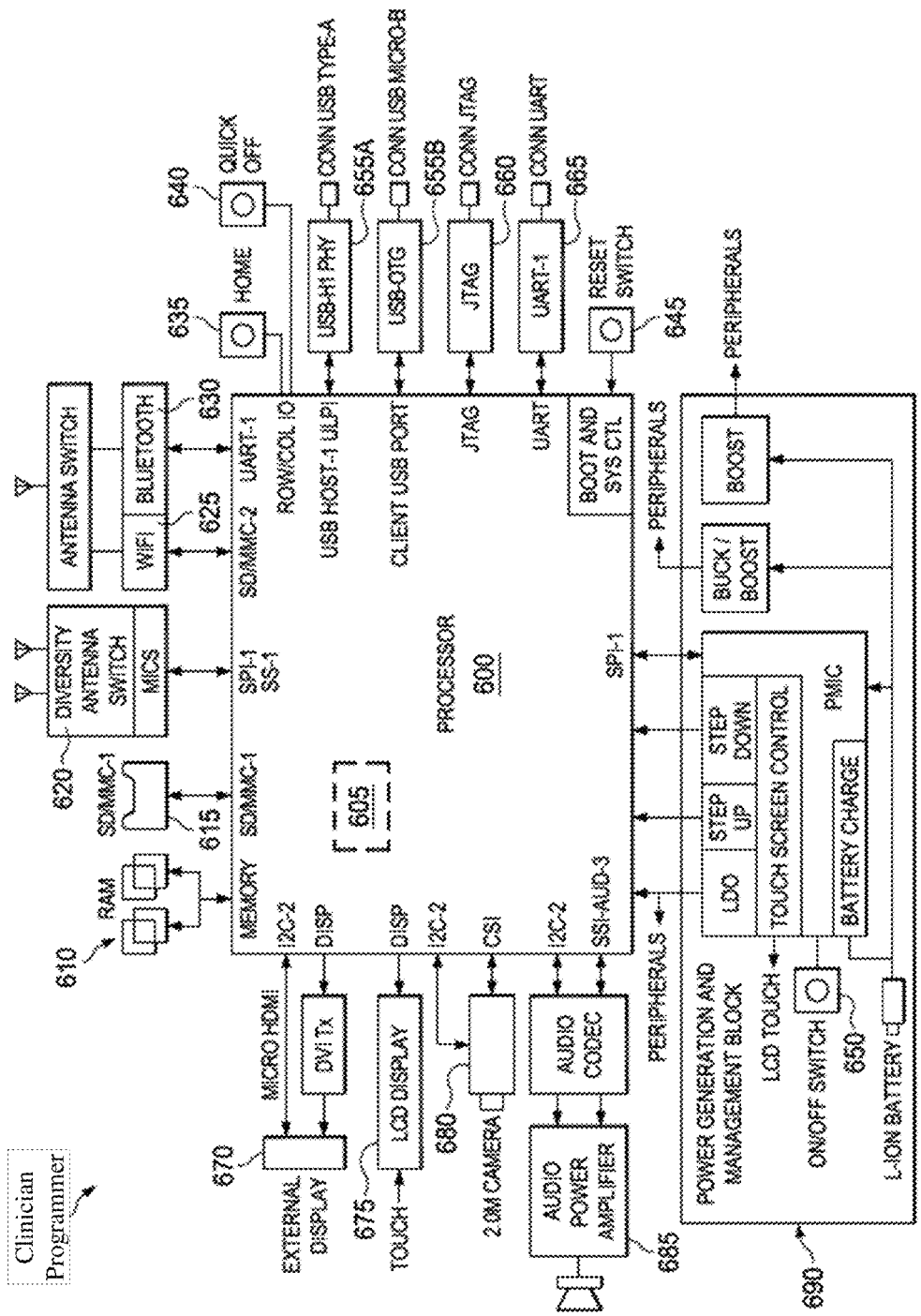
FIG. 9 is a simplified block diagram of an electronic programmer according to various aspects of the present disclosure.

FIG. 9 shows a block diagram of one embodiment of the electronic programmer (CP) discussed herein. For example, the electronic programmer may be a clinician programmer (CP) configured to generate and display the impedance information discussed above. It is understood, however, that alternative embodiments of the electronic programmer may be used to perform these representations as well.

The CP includes a printed circuit board ("PCB") that is populated with a plurality of electrical and electronic components that provide power, operational control, and protection to the CP. With reference to FIG. 9, the CP includes a processor 600. The processor 600 controls the CP. In one construction, the processor 600 is an applications processor model i.MX515 available from Free scale Semiconductor®. More specifically, the i.MX515 applications processor has internal instruction and data caches, multimedia capabilities, external memory interfacing, and interfacing flexibility. Further information regarding the i.MX515 applications processor can be found in, for example, the "IMX510EC, Rev. 4" data sheet dated August 2010 and published by Free scale Semiconductor® at www.freescale.com. The content of the data sheet is incorporated herein by reference. Of course, other processing units, such as other microprocessors, microcontrollers, digital signal processors, etc., can be used in place of the processor 600.

The CP includes memory, which can be internal to the processor 600 (e.g., memory 605), external to the processor 600 (e.g., memory 610), or a combination of both. Exemplary memory include a read-only memory ("ROM"), a random access memory ("RAM"), an electrically erasable programmable read-only memory ("EEPROM"), a flash memory, a hard disk, or another suitable magnetic, optical, physical, or electronic memory device. The processor 600 executes software that is capable of being stored in the RAM (e.g., during execution), the ROM (e.g., on a generally permanent basis), or another non-transitory computer readable medium such as another memory or a disc. The CP also includes input/output ("I/O") systems that include routines for transferring information between components within the processor 600 and other components of the CP or external to the CP.

Software included in the implementation of the CP is stored in the memory 605 of the processor 600, RAM 610, ROM 615, or external to the CP. The software includes, for example, firmware, one or more applications, program data, one or more program modules, and other executable instructions. The processor 600 is configured to retrieve from memory and execute, among other things, instructions related to the control processes and methods described below for the CP.

One memory shown in FIG. 9 is memory 610, which may be a double data rate (DDR2) synchronous dynamic random access memory (SDRAM) for storing data relating to and captured during the operation of the CP. In addition, a secure digital (SD) multimedia card (MMC) may be coupled to the CP for transferring data from the CP to the memory card via slot 615. Of course, other types of data storage devices may be used in place of the data storage devices shown in FIG. 9.

The CP includes multiple bi-directional radio communication capabilities. Specific wireless portions included with the CP are a Medical Implant Communication Service (MICS) bi-directional radio communication portion 620, a Wi-Fi bi-directional radio communication portion 625, and a Bluetooth bi-directional radio communication portion 630. The MICS portion 620 includes a MICS communication interface, an antenna switch, and a related antenna, all of which allows wireless communication using the MICS specification. The Wi-Fi portion 625 and Bluetooth portion 630 include a Wi-Fi communication interface, a Bluetooth communication interface, an antenna switch, and a related antenna all of which allows wireless communication following the Wi-Fi Alliance standard and Bluetooth Special Interest Group standard. Of course, other wireless local area network (WLAN) standards and wireless personal area networks (WPAN) standards can be used with the CP.

The CP includes three hard buttons: a "home" button 635 for returning the CP to a home screen for the device, a "quick off" button 640 for quickly deactivating stimulation IPG, and a "reset" button 645 for rebooting the CP. The CP also includes an "ON/OFF" switch 650, which is part of the power generation and management block (discussed below).

The CP includes multiple communication portions for wired communication. Exemplary circuitry and ports for receiving a wired connector include a portion and related port for supporting universal serial bus (USB) connectivity 655, including a Type A port and a Micro-B port; a portion and related port for supporting Joint Test Action Group (JTAG) connectivity 660, and a portion and related port for supporting universal asynchronous receiver/transmitter (UART) connectivity 665. Of course, other wired communication standards and connectivity can be used with or in place of the types shown in FIG. 9.

Another device connectable to the CP, and therefore supported by the CP, is an external display. The connection to the external display can be made via a micro High-Definition Multimedia Interface (HDMI) 670, which provides a compact audio/video interface for transmitting uncompressed digital data to the external display. The use of the HDMI connection 670 allows the CP to transmit video (and audio) communication to an external display. This may be beneficial in situations where others (e.g., the surgeon) may want to view the information being viewed by the healthcare professional. The surgeon typically has no visual access to the CP in the operating room unless an external screen is provided. The HDMI connection 670 allows the surgeon to view information from the CP, thereby allowing greater communication between the clinician and the surgeon. For a specific example, the HDMI connection 670 can broadcast a high definition television signal that allows the surgeon to view the same information that is shown on the LCD (discussed below) of the CP.

The CP includes a touch screen I/O device 675 for providing a user interface with the clinician. The touch screen display 675 can be a liquid crystal display (LCD) having a resistive, capacitive, or similar touch-screen technology. It is envisioned that multitouch capabilities can be used with the touch screen display 675 depending on the type of technology used.

The CP includes a camera 680 allowing the device to take pictures or video. The resulting image files can be used to document a procedure or an aspect of the procedure. Other devices can be coupled to the CP to provide further information, such as scanners or RFID detection. Similarly, the CP includes an audio portion 685 having an audio codec circuit, audio power amplifier, and related speaker for providing audio communication to the user, such as the clinician or the surgeon.

The CP further includes a power generation and management block 690. The power block 690 has a power source (e.g., a lithium-ion battery) and a power supply for providing multiple power voltages to the processor, LCD touch screen, and peripherals.

In one embodiment, the CP is a handheld computing tablet with touch screen capabilities. The tablet is a portable personal computer with a touch screen, which is typically the primary input device. However, an external keyboard or mouse can be attached to the CP. The tablet allows for mobile functionality not associated with even typical laptop personal computers. The hardware may include a Graphical Processing Unit (GPU) in order to speed up the user experience. An Ethernet port (not shown in FIG. 9) may also be included for data transfer.

It is understood that a patient programmer may be implemented in a similar manner as the clinician programmer shown in FIG. 9.

Figure 10:
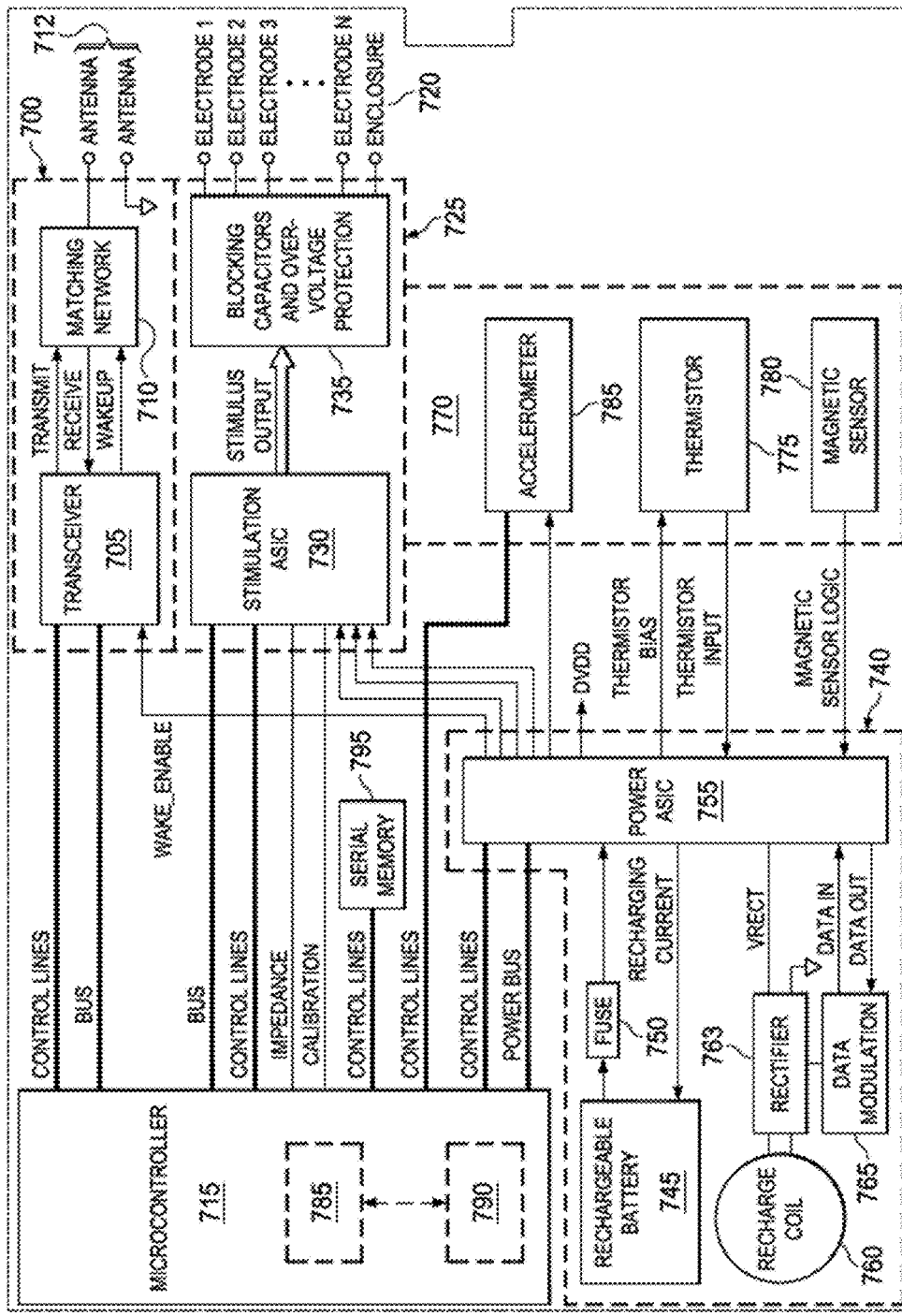
FIG. 10 is a simplified block diagram of an implantable medical device according to various aspects of the present disclosure.

FIG. 10 shows a block diagram of one embodiment of an implantable medical device. In the embodiment shown in FIG. 10, the implantable medical device includes an implantable pulse generator (IPG). The IPG includes a printed circuit board ("PCB") that is populated with a plurality of electrical and electronic components that provide power, operational control, and protection to the IPG. With reference to FIG. 10, the IPG includes a communication portion 700 having a transceiver 705, a matching network 710, and antenna 712. The communication portion 700 receives power from a power ASIC (discussed below), and communicates information to/from the microcontroller 715 and a device (e.g., the CP) external to the IPG. For example, the IPG can provide bi-direction radio communication capabilities, including Medical Implant Communication Service (MICS) bi-direction radio communication following the MICS specification.

The IPG provides stimuli to electrodes of an implanted medical electrical lead (not illustrated herein). As shown in FIG. 10, N electrodes are connected to the IPG. In addition, the enclosure or housing 720 of the IPG can act as an electrode. The stimuli are provided by a stimulation portion 225 in response to commands from the microcontroller 215. The stimulation portion 725 includes a stimulation application specific integrated circuit (ASIC) 730 and circuitry including blocking capacitors and an over-voltage protection circuit. As is well known, an ASIC is an integrated circuit customized for a particular use, rather than for general purpose use. ASICs often include processors, memory blocks including ROM, RAM, EEPROM, FLASH, etc. The stimulation ASIC 730 can include a processor, memory, and firmware for storing preset pulses and protocols that can be selected via the microcontroller 715. The providing of the pulses to the electrodes is controlled through the use of a waveform generator and amplitude multiplier of the stimulation ASIC 730, and the blocking capacitors and overvoltage protection circuitry 735 of the stimulation portion 725, as is known in the art. The stimulation portion 725 of the IPG receives power from the power ASIC (discussed below). The stimulation ASIC 730 also provides signals to the microcontroller 715. More specifically, the stimulation ASIC 730 can provide impedance values for the channels associated with the electrodes, and also communicate calibration information with the microcontroller 715 during calibration of the IPG.

The IPG also includes a power supply portion 740. The power supply portion includes a rechargeable battery 745, fuse 750, power ASIC 755, recharge coil 760, rectifier 763 and data modulation circuit 765. The rechargeable battery 745 provides a power source for the power supply portion 740. The recharge coil 760 receives a wireless signal from the PPC. The wireless signal includes an energy that is converted and conditioned to a power signal by the rectifier 763. The power signal is provided to the rechargeable battery 745 via the power ASIC 755. The power ASIC 755 manages the power for the IPG. The power ASIC 755 provides one or more voltages to the other electrical and electronic circuits of the IPG. The data modulation circuit 765 controls the charging process.

The IPG also includes a magnetic sensor 780. The magnetic sensor 780 provides a "hard" switch upon sensing a magnet for a defined period. The signal from the magnetic sensor 780 can provide an override for the IPG if a fault is occurring with the IPG and is not responding to other controllers.

The IPG is shown in FIG. 10 as having a microcontroller 715. Generally speaking, the microcontroller 715 is a controller for controlling the IPG. The microcontroller 715 includes a suitable programmable portion 785 (e.g., a microprocessor or a digital signal processor), a memory 790, and a bus or other communication lines. An exemplary microcontroller capable of being used with the IPG is a model MSP430 ultra-low power, mixed signal processor by Texas Instruments. More specifically, the MSP430 mixed signal processor has internal RAM and flash memories, an internal clock, and peripheral interface capabilities. Further information regarding the MSP430 mixed signal processor can be found in, for example, the "MSP430G2×32, MSP430G2×02 MIXED SIGNAL MICROCONTROLLER" data sheet; dated December 2010, published by Texas Instruments at www.ti.com; the content of the data sheet being incorporated herein by reference.

The IPG includes memory, which can be internal to the control device (such as memory 790), external to the control device (such as serial memory 795), or a combination of both. Exemplary memory include a read-only memory ("ROM"), a random access memory ("RAM"), an electrically erasable programmable read-only memory ("EEPROM"), a flash memory, a hard disk, or another suitable magnetic, optical, physical, or electronic memory device. The programmable portion 785 executes software that is capable of being stored in the RAM (e.g., during execution), the ROM (e.g., on a generally permanent basis), or another non-transitory computer readable medium such as another memory or a disc.

Software included in the implementation of the IPG is stored in the memory 790. The software includes, for example, firmware, one or more applications, program data, one or more program modules, and other executable instructions. The programmable portion 785 is configured to retrieve from memory and execute, among other things, instructions related to the control processes and methods described below for the IPG. For example, the programmable portion 285 is configured to execute instructions retrieved from the memory 790 for sweeping the electrodes in response to a signal from the CP.

Figure 11:
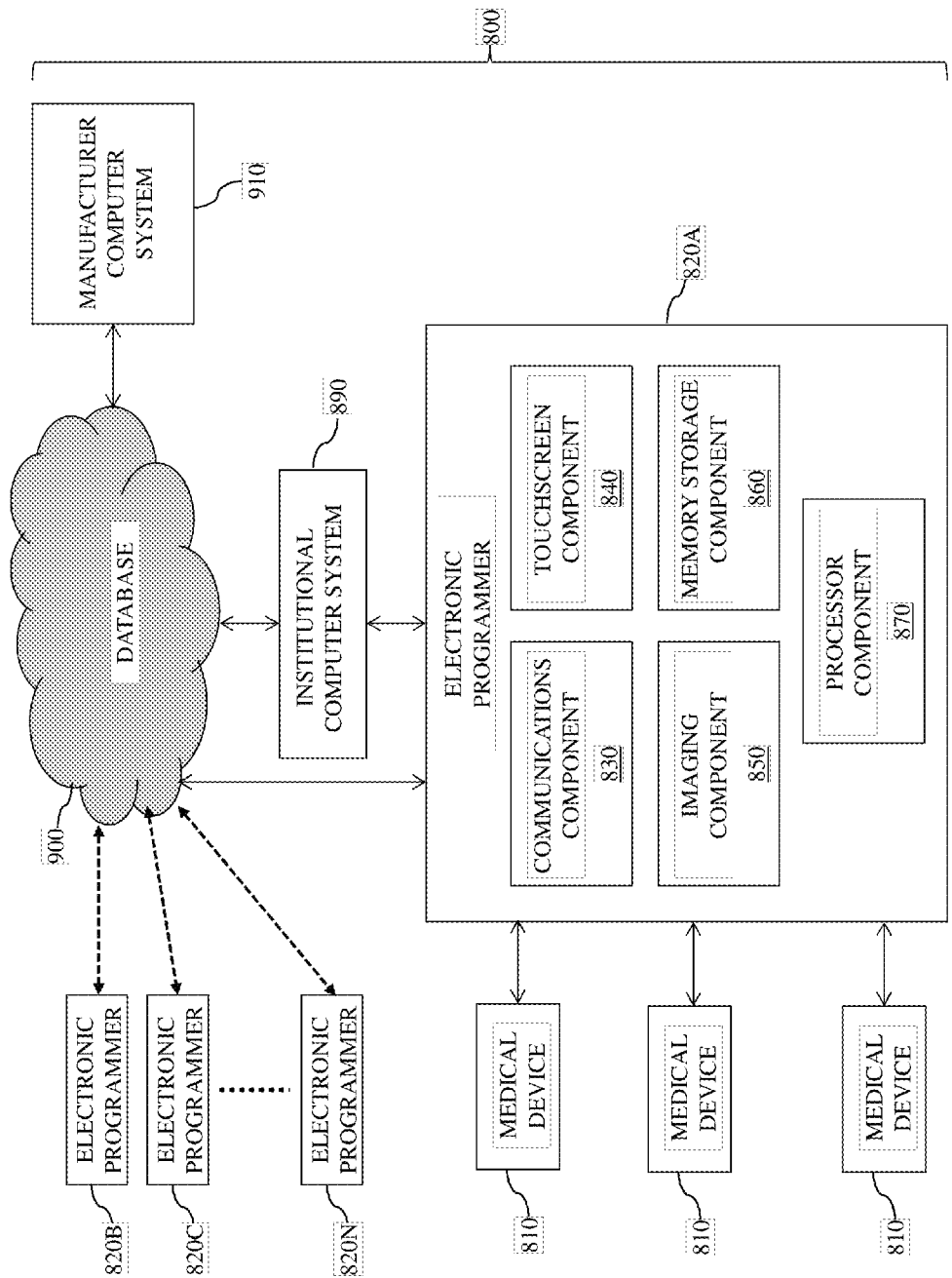
FIG. 11 is a simplified block diagram of a medical system/infrastructure according to various aspects of the present disclosure.

Referring now to FIG. 11, a simplified block diagram of a medical infrastructure 800 (which may also be considered a medical system) is illustrated according to various aspects of the present disclosure. The medical infrastructure 800 includes a plurality of medical devices 810. These medical devices 810 may each be a programmable medical device (or parts thereof) that can deliver a medical therapy to a patient. In some embodiments, the medical devices 810 may include a device of the neurostimulator system discussed above with reference to FIG. 1. For example, the medical devices 810 may be a pulse generator (e.g., the IPG discussed above with reference to FIG. 10), an implantable lead, a charger, or portions thereof. It is understood that each of the medical devices 810 may be a different type of medical device. In other words, the medical devices 810 need not be the same type of medical device.

The medical infrastructure 800 also includes a plurality of electronic programmers 820. For sake of illustration, one of these electronic programmers 820A is illustrated in more detail and discussed in detail below. Nevertheless, it is understood that each of the electronic programmers 820 may be implemented similar to the electronic programmer 820A.

In some embodiments, the electronic programmer 820A may be a clinician programmer, for example the clinician programmer discussed above with reference to FIG. 9. In other embodiments, the electronic programmer 820A may be a patient programmer or another similar programmer. In further embodiments, it is understood that the electronic programmer may be a tablet computer. In any case, the electronic programmer 820A is configured to program the stimulation parameters of the medical devices 810 so that a desired medical therapy can be delivered to a patient.

The electronic programmer 820A contains a communications component 830 that is configured to conduct electronic communications with external devices. For example, the communications device 830 may include a transceiver. The transceiver contains various electronic circuitry components configured to conduct telecommunications with one or more external devices. The electronic circuitry components allow the transceiver to conduct telecommunications in one or more of the wired or wireless telecommunications protocols, including communications protocols such as IEEE 802.11 (Wi-Fi), IEEE 802.15 (Bluetooth), GSM, CDMA, LTE, WIMAX, DLNA, HDMI, Medical Implant Communication Service (MICS), etc. In some embodiments, the transceiver includes antennas, filters, switches, various kinds of amplifiers such as low-noise amplifiers or power amplifiers, digital-to-analog (DAC) converters, analog-to-digital (ADC) converters, mixers, multiplexers and demultiplexers, oscillators, and/or phase-locked loops (PLLs). Some of these electronic circuitry components may be integrated into a single discrete device or an integrated circuit (IC) chip.

The electronic programmer 820A contains a touchscreen component 840. The touchscreen component 840 may display a touch-sensitive graphical user interface that is responsive to gesture-based user interactions. The touch-sensitive graphical user interface may detect a touch or a movement of a user's finger(s) on the touchscreen and interpret these user actions accordingly to perform appropriate tasks. The graphical user interface may also utilize a virtual keyboard to receive user input. In some embodiments, the touch-sensitive screen may be a capacitive touchscreen. In other embodiments, the touch-sensitive screen may be a resistive touchscreen.

It is understood that the electronic programmer 820A may optionally include additional user input/output components that work in conjunction with the touchscreen component 840 to carry out communications with a user. For example, these additional user input/output components may include physical and/or virtual buttons (such as power and volume buttons) on or off the touch-sensitive screen, physical and/or virtual keyboards, mouse, track balls, speakers, microphones, light-sensors, light-emitting diodes (LEDs), communications ports (such as USB or HDMI ports), joy-sticks, etc.

The electronic programmer 820A contains an imaging component 850. The imaging component 850 is configured to capture an image of a target device via a scan. For example, the imaging component 850 may be a camera in some embodiments. The camera may be integrated into the electronic programmer 820A. The camera can be used to take a picture of a medical device, or scan a visual code of the medical device, for example its barcode or Quick Response (QR) code.

The electronic programmer contains a memory storage component 860. The memory storage component 860 may include system memory, (e.g., RAM), static storage 608

(e.g., ROM), or a disk drive (e.g., magnetic or optical), or any other suitable types of computer readable storage media. For example, some common types of computer readable media may include floppy disk, flexible disk, hard disk, magnetic tape, any other magnetic medium, CD-ROM, any other optical medium, RAM, PROM, EPROM, FLASH-EPROM, any other memory chip or cartridge, or any other medium from which a computer is adapted to read. The computer readable medium may include, but is not limited to, non-volatile media and volatile media. The computer readable medium is tangible, concrete, and non-transitory. Logic (for example in the form of computer software code or computer instructions) may be encoded in such computer readable medium. In some embodiments, the memory storage component 860 (or a portion thereof) may be configured as a local database capable of storing electronic records of medical devices and/or their associated patients.

The electronic programmer contains a processor component 870. The processor component 870 may include a central processing unit (CPU), a graphics processing unit (GPU) a micro-controller, a digital signal processor (DSP), or another suitable electronic processor capable of handling and executing instructions. In various embodiments, the processor component 870 may be implemented using various digital circuit blocks (including logic gates such as AND, OR, NAND, NOR, XOR gates, etc.) along with certain software code. In some embodiments, the processor component 870 may execute one or more sequences computer instructions contained in the memory storage component 860 to perform certain tasks.

It is understood that hard-wired circuitry may be used in place of (or in combination with) software instructions to implement various aspects of the present disclosure. Where applicable, various embodiments provided by the present disclosure may be implemented using hardware, software, or combinations of hardware and software. Also, where applicable, the various hardware components and/or software components set forth herein may be combined into composite components comprising software, hardware, and/or both without departing from the spirit of the present disclosure. Where applicable, the various hardware components and/or software components set forth herein may be separated into sub-components comprising software, hardware, or both without departing from the scope of the present disclosure. In addition, where applicable, it is contemplated that software components may be implemented as hardware components and vice-versa.

It is also understood that the electronic programmer 820A is not necessarily limited to the components 830-870 discussed above, but it may further include additional components that are used to carry out the programming tasks. These additional components are not discussed herein for reasons of simplicity. It is also understood that the medical infrastructure 800 may include a plurality of electronic programmers similar to the electronic programmer 820A discussed herein, but they are not illustrated in FIG. 11 for reasons of simplicity.

The medical infrastructure 800 also includes an institutional computer system 890. The institutional computer system 890 is coupled to the electronic programmer 820A. In some embodiments, the institutional computer system 890 is a computer system of a healthcare institution, for example a hospital. The institutional computer system 890 may include one or more computer servers and/or client terminals that may each include the necessary computer hardware and software for conducting electronic communications and performing programmed tasks. In various embodiments, the institutional computer system 890 may include communications devices (e.g., transceivers), user input/output devices, memory storage devices, and computer processor devices that may share similar properties with the various components 830-870 of the electronic programmer 820A discussed above. For example, the institutional computer system 890 may include computer servers that are capable of electronically communicating with the electronic programmer 820A through the MICS protocol or another suitable networking protocol.

The medical infrastructure 800 includes a database 900. In various embodiments, the database 900 is a remote database—that is, located remotely to the institutional computer system 890 and/or the electronic programmer 820A. The database 900 is electronically or communicatively (for example through the Internet) coupled to the institutional computer system 890 and/or the electronic programmer. In some embodiments, the database 900, the institutional computer system 890, and the electronic programmer 820A are parts of a cloud-based architecture. In that regard, the database 900 may include cloud-based resources such as mass storage computer servers with adequate memory resources to handle requests from a variety of clients. The institutional computer system 890 and the electronic programmer 820A (or their respective users) may both be considered clients of the database 900. In certain embodiments, the functionality between the cloud-based resources and its clients may be divided up in any appropriate manner. For example, the electronic programmer 820A may perform basic input/output interactions with a user, but a majority of the processing and caching may be performed by the cloud-based resources in the database 900. However, other divisions of responsibility are also possible in various embodiments.

According to the various aspects of the present disclosure, the impedance information may be uploaded from the electronic programmer 820A to the database 900. The impedance information saved in the database 900 may thereafter be downloaded by any of the other electronic programmers 820B-820N communicatively coupled to it, assuming the user of these programmers has the right login permissions.

The database 900 may also include a manufacturer's database in some embodiments. It may be configured to manage an electronic medical device inventory, monitor manufacturing of medical devices, control shipping of medical devices, and communicate with existing or potential buyers (such as a healthcare institution). For example, communication with the buyer may include buying and usage history of medical devices and creation of purchase orders. A message can be automatically generated when a client (for example a hospital) is projected to run out of equipment, based on the medical device usage trend analysis done by the database. According to various aspects of the present disclosure, the database 900 is able to provide these functionalities at least in part via communication with the electronic programmer 820A and in response to the data sent by the electronic programmer 820A. These functionalities of the database 900 and its communications with the electronic programmer 820A will be discussed in greater detail later.

The medical infrastructure 800 further includes a manufacturer computer system 910. The manufacturer computer system 910 is also electronically or communicatively (for example through the Internet) coupled to the database 900. Hence, the manufacturer computer system 910 may also be considered a part of the cloud architecture. The computer system 910 is a computer system of medical device manufacturer, for example a manufacturer of the medical devices 810 and/or the electronic programmer 820A.

In various embodiments, the manufacturer computer system 910 may include one or more computer servers and/or client terminals that each includes the necessary computer hardware and software for conducting electronic communications and performing programmed tasks. In various embodiments, the manufacturer computer system 910 may include communications devices (e.g., transceivers), user input/output devices, memory storage devices, and computer processor devices that may share similar properties with the various components 830-870 of the electronic programmer 820A discussed above. Since both the manufacturer computer system 910 and the electronic programmer 820A are coupled to the database 900, the manufacturer computer system 910 and the electronic programmer 820A can conduct electronic communication with each other.

Figure 12A:
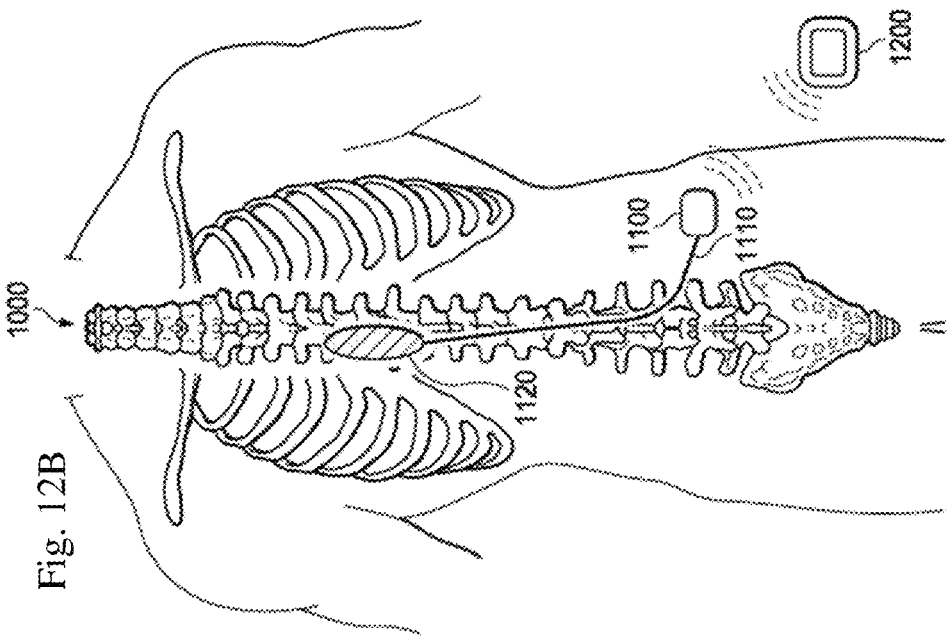
FIGS. 12A and 12B are side and posterior views of a human spine, respectively.
Figure 12B:
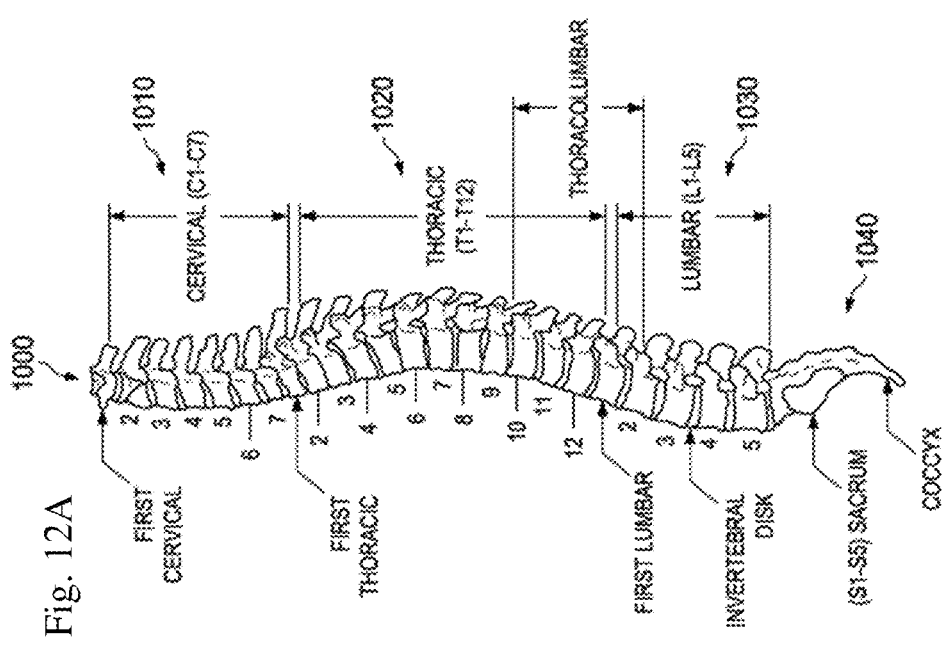

FIG. 12A is a side view of a spine 1000, and FIG. 12B is a posterior view of the spine 1000. The spine 1000 includes a cervical region 1010, a thoracic region 1020, a lumbar region 1030, and a sacrococcygeal region 1040. The cervical region 1010 includes the top 7 vertebrae, which may be designated with C1-C7. The thoracic region 1020 includes the next 12 vertebrae below the cervical region 1010, which may be designated with T1-T12. The lumbar region 1030 includes the final 5 "true" vertebrae, which may be designated with L1-L5. The sacrococcygeal region 1040 includes 9 fused vertebrae that make up the sacrum and the coccyx. The fused vertebrae of the sacrum may be designated with S1-S5.

Neural tissue (not illustrated for the sake of simplicity) branch off from the spinal cord through spaces between the vertebrae. The neural tissue can be individually and selectively stimulated in accordance with various aspects of the present disclosure. For example, referring to FIG. 12B, an IPG device 1100 is implanted inside the body. The IPG device 1100 may include a neurostimulator device. A conductive lead 1110 is electrically coupled to the circuitry inside the IPG device 1100. The conductive lead 1110 may be removably coupled to the IPG device 1100 through a connector, for example. A distal end of the conductive lead 1110 is attached to one or more electrodes 1120. The electrodes 1120 are implanted adjacent to a desired nerve tissue in the thoracic region 1020. Using well-established and known techniques in the art, the distal end of the lead 1110 with its accompanying electrodes may be positioned along or near the epidural space of the spinal cord. It is understood that although only one conductive lead 1110 is shown herein for the sake of simplicity, more than one conductive lead 1110 and corresponding electrodes 1120 may be implanted and connected to the IPG device 1100.

The electrodes 1120 deliver current drawn from the current sources in the IPG device 1100, therefore generating an electric field near the neural tissue. The electric field stimulates the neural tissue to accomplish its intended functions. For example, the neural stimulation may alleviate pain in an embodiment. In other embodiments, a stimulator may be placed in different locations throughout the body and may be programmed to address a variety of problems, including for example but without limitation; prevention or reduction of epileptic seizures, weight control or regulation of heart beats.

It is understood that the IPG device 1100, the lead 1110, and the electrodes 1120 may be implanted completely inside the body, may be positioned completely outside the body or may have only one or more components implanted within the body while other components remain outside the body.

When they are implanted inside the body, the implant location may be adjusted (e.g., anywhere along the spine 1000) to deliver the intended therapeutic effects of spinal cord electrical stimulation in a desired region of the spine. Furthermore, it is understood that the IPG device 1100 may be controlled by a patient programmer or a clinician programmer 1200, the implementation of which may be similar to the clinician programmer shown in FIG. 9.

The foregoing has outlined features of several embodiments so that those skilled in the art may better understand the detailed description that follows. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. A method of displaying impedance information of an implantable medical device, the method comprising:
   receiving a plurality of impedance values over a period of time for each of a plurality of channels, wherein the channels each include an electrode contact on an implantable lead;
   determining, from the plurality of impedance values, a respective worst case impedance value during the period of time for each of the channels, wherein the respective worst case impedance value is an impedance value that has a greatest amount of deviation from either a specified upper threshold or a specified lower threshold;
   displaying, via a graphical user interface of a clinician programmer, a graph that illustrates a variation of the impedance values over at least a portion of the period of time for one or more of the channels; and
   displaying, via the graphical user interface of the clinician programmer, a visual landscape that is representative of the respective worst case impedance value for each of the plurality of channels.

2. The method of claim 1, wherein:
   the displaying of the visual landscape comprises displaying a plurality of icons that are each associated with a respective one of the channels; and
   a visual characteristic of each of the icons indicates an impedance value range within which the respective worst case impedance value of the channel associated with the icon falls.

3. The method of claim 1, wherein the displaying of the graph comprises displaying, concurrently on the graph:
   a first plot representing the variation of the impedance values for a first one of the channels over the period of time; and
   a second plot representing the variation of the impedance values for a second one of the channels over the period of time.

4. The method of claim 1, further comprising: displaying, separately from the displaying of the visual landscape, the impedance values for at least a subset of the channels, wherein each of the impedance values is measured with respect to one of: electrical ground and each of the rest of the channels in the subset.

5. The method of claim 1, further comprising: displaying a window showing one or more user-configurable settings for generating an electrical pulse used to perform impedance measurements for the plurality of channels.

6. The method of claim 1, wherein the displaying of the graph is performed such that the graph includes a X-axis representing time and a Y-axis representing impedance, and wherein at least one of the X-axis and the Y-axis is zoom-able or scrollable.

7. The method of claim 1, further comprising: automatically generating an alert when the worst case impedance value for one of the channels is outside of a predefined range.

8. The method of claim 1, wherein the receiving of the plurality of impedance values and the determining the worst case impedance value are performed via the clinician programmer.

9. The method of claim 1, further comprising: displaying, separately from the displaying of the graph and the visual landscape, the impedance values for at least a subset of the channels, the impedance values being measured with respect to a source channel.

10. The method of claim 1, wherein the visual landscape comprises different colors.

11. An electronic device for displaying impedance information of an implantable medical device, the electronic device comprising:
a touch-sensitive graphical user interface;
a memory storage component configured to store programming code; and
a computer processor configured to execute the programming code to perform the following tasks:
receiving a plurality of impedance values over a period of time for each of a plurality of channels, wherein the channels each include an electrode contact on an implantable lead;
determining, from the plurality of impedance values, a respective worst case impedance value during the period of time for each of the channels, wherein the respective worst case impedance value is an impedance value that has a greatest amount of deviation from either a specified upper threshold or a specified lower threshold;
displaying, via the touch-sensitive graphical user interface, a graph that illustrates a variation of the impedance values over at least a portion of the period of time for one or more of the plurality of channels; and
displaying, via the touch-sensitive graphical user interface, a visual landscape that is representative of the respective worst case impedance values for each of the plurality of channels.

12. The electronic device of claim 11, wherein:
the displaying of the visual landscape comprises displaying a plurality of icons that are each associated with a respective one of the channels; and
a visual characteristic of each of the icons indicates an impedance value range within which the respective worse case impedance value of the channel associated with the icon falls.

13. The electronic device of claim 11, wherein the displaying of the graph comprises displaying, concurrently on the graph:
a first plot representing the variation of the impedance values for a first one of the channels over the period of time; and
a second plot representing the variation of the impedance values for a second one of the channels over the period of time.

14. The electronic device of claim 11, wherein the tasks further comprise:
displaying, separately from the displaying of the visual landscape, the impedance values for at least a subset of the channels, wherein each of the impedance values is measured with respect to one of: electrical ground and each of the rest of the channels in the subset;
displaying a window showing one or more user-configurable settings for generating an electrical pulse used to perform impedance measurements for the plurality of channels; and
automatically generating an alert when the worst case impedance value for one of the channels is outside of a predefined range.

15. The electronic device of claim 11, wherein the displaying of the graph is performed such that the graph includes a X-axis representing time and a Y-axis representing impedance, and wherein at least one of the X-axis and the Y-axis is zoom-able or scrollable.

16. A medical system, comprising:
an implantable lead configured to deliver electrical stimulation to a patient via one or more of a plurality of channels located on the implantable lead; and
a portable electronic programmer on which a graphical user interface is implemented, wherein, via the graphical user interface, the portable electronic programmer is configured to:
receive a plurality of impedance values over a period of time for each of the plurality of channels;
determining, from the plurality of impedance values, a respective worst case impedance value during the period of time for each of the channels, wherein the respective worst case impedance value is an impedance value that has a greatest amount of deviation from either a specified upper threshold or a specified lower threshold;
display, via the graphical user interface, a graph that illustrates a variation of the impedance values over at least a portion of the period of time for one or more of the plurality of channels; and
display, via the graphical user interface, a visual landscape that is representative of the respective worst case impedance values for each of the plurality of channels.

17. The medical system of claim 16, wherein:
the visual landscape includes a plurality of icons that are each associated with a respective one of the channels; and
a visual characteristic of each of the icons indicates an impedance value range within which the respective worst case impedance value of the channel associated with the icon falls.

18. The medical system of claim 16, wherein the graphical user interface is configured to display, concurrently on the graph:
a first plot representing the variation of the impedance values for a first one of the channels over the period of time; and
a second plot representing the variation of the impedance values for a second one of the channels over the period of time.

19. The medical system of claim 16, wherein the graphical user interface is further configured to:
display, separately from the visual landscape, the impedance values for at least a subset of the channels, wherein each of the impedance values is measured with respect to one of: electrical ground and each of the rest of the channels in the subset;

display a window showing one or more user-configurable settings for generating an electrical pulse used to perform impedance measurements for the plurality of channels; and automatically generate an alert when the worst case impedance value for one of the channels is outside of a predefined range.

20. The medical system of claim 16, wherein the graph includes a X-axis representing time and a Y-axis representing impedance, and wherein at least one of the X-axis and the Y-axis is zoom-able or scrollable.

* * * * *